US007795020B2

(12) United States Patent
Lawman et al.

(10) Patent No.: US 7,795,020 B2
(45) Date of Patent: *Sep. 14, 2010

(54) TUMOR CELL VACCINES

(75) Inventors: Michael J. P. Lawman, Tampa, FL (US); Patricia Lawman, Tampa, FL (US)

(73) Assignee: Morphogenesis, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/049,634

(22) Filed: Mar. 17, 2008

(65) Prior Publication Data

US 2008/0166379 A1 Jul. 10, 2008

Related U.S. Application Data

(63) Continuation-in-part of application No. 10/964,471, filed on Oct. 13, 2004, now Pat. No. 7,348,015, which is a continuation-in-part of application No. 10/652,578, filed on Aug. 29, 2003, now Pat. No. 7,094,603, which is a continuation-in-part of application No. 09/950,374, filed on Sep. 10, 2001, now abandoned, which is a continuation of application No. 09/394,226, filed on Sep. 13, 1999, now abandoned, which is a continuation of application No. PCT/US99/00787, filed on Jan. 14, 1999.

(60) Provisional application No. 60/071,497, filed on Jan. 14, 1998.

(51) Int. Cl.
  *C12N 5/00* (2006.01)
  *C12N 15/00* (2006.01)
  *C12N 5/071* (2006.01)
(52) U.S. Cl. ................. 435/325; 435/455; 435/366
(58) Field of Classification Search ................. 435/325, 435/366, 455
  See application file for complete search history.

(56) References Cited

U.S. PATENT DOCUMENTS

| 5,736,388 | A | 4/1998 | Chada et al. |
| 6,774,119 | B1 | 8/2004 | Wechsler et al. |
| 2005/0106130 | A1 | 5/2005 | Lawman et al. |
| 2008/0095789 | A1* | 4/2008 | Kiessling et al. ......... 424/185.1 |

FOREIGN PATENT DOCUMENTS

| EP | 0569678 | 11/1993 |
| WO | WO 93/24136 | 12/1993 |
| WO | WO 94/21808 | 9/1994 |
| WO | WO 95/00178 | 1/1995 |
| WO | WO 95/13092 | 5/1995 |
| WO | WO 96/29093 | 9/1996 |
| WO | WO 96/36366 | 11/1996 |
| WO | WO 97/00085 | 1/1997 |
| WO | WO 99/36433 | 7/1999 |

OTHER PUBLICATIONS

Dale et la., Recombinant tetravalent group A streptococcal M protein vaccine J Immunol. Aug. 15, 1993;151(4):2188-94.*
Watson et al., Recombinant DNA, Second Edition, 2nd ed. Distributed by W. H. Freeman and Company, 2001. pp. 153-155.*
Hollingshead,et al., Molecular evolution of a multigene family in group A streptococci, Molecular Biology and Evolution, vol. 11, 208-219, 1994.*
National Cancer Institute, Fact Sheet Cancer Vaccines 2009, pp. 1-17.*
Rudinger, J., "Characteristics of the amino acids as components of a peptide hormone sequence",in Peptide Hormones, University Park Press: Baltimore, MD, pp. 1-7, 1976.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.*
Voet, Biochemistry John Wiley and Sons, 1990, pp. 126-128.*
Kimchi-Sarfaty Cet al., A "silent" polymorphism in the MDR1 gene changes substrate specificity.Science. Jan. 26, 2007;315(5811):525-8.*
Avery, A. C. et al. "Activation of T Cells by Superantigen in Class II-Negative Mice" *J. Immunol.*, 1994, pp. 4855-4861, vol. 153.
Banchereau, J. et al. "Dendritic Cells and the Control of Immunity" *Nature*, 1998, pp. 245-252, vol. 392.
Barratt-Boyes, S. M. et al. "Studies in a Chimpanzee Model of Dendritic Cell-Based Cancer Vaccines" Proceedings of the 87th, Annual Meeting of the American Association for Cancer, 1996, XP002039146 (abstract only).
Boyle, Michael D. P. et al. "Analysis of Genes Encoding Two Unique Type IIa Immunoglobulin G-Binding Proteins Expressed by a Single Group A Streptococcal Isolate" *Infection and Immunology*, 1994, pp. 1336-1347, vol. 62, No. 4.
Boyle, Michael D. P. et al. "Characterization of A Gene Coding for A Type IIo Bacterial IgG-Binding Protein" *Molecular Immunology*, 1995, pp. 669-678, vol. 32, No. 9.
Dellabona, Paolo et al. "Superantigens Interact With MHC Class II Molecules Outside of the Antigen Groove" *Cell*, 1990, pp. 1115-1121, vol. 62.
Dohlsten, M. et al. "Monoclonal Antibody-Targeted Superantigens: A Different Class of Anti-Tumor Agents" *Proc. Natl. Acad. Sci. USA*, 1991, pp. 9287-9291, vol. 88.
Dohlsten, M. et al. "Human Major Histocompatibility Complex Class II-Negative Colon Carcinoma Cells Present Staphylococcal Superantigens to Cytotoxic T Lymphocytes: Evidence for a Novel Enterotoxin Receptor" *Eur. J. Immunol.*, 1991, pp. 1229-1233, vol. 21.

(Continued)

*Primary Examiner*—Maria Leavitt
(74) *Attorney, Agent, or Firm*—Saliwanchik, Lloyd & Saliwanchik

(57) ABSTRACT

An effective cancer cell vaccine for canines has been developed. The vaccine is prepared from autologous lymphoma cells transfected with emm55. Once an animal is vaccinated, the expressed Emm55 antigen stimulates an immunogenic response to the tumor cells resulting in significantly increased survival, strong autologous and cross reactive humoral and cell mediated responses in several breeds of dogs diagnosed with later stage lymphomas.

9 Claims, 6 Drawing Sheets

OTHER PUBLICATIONS

Dohlsten, M. et al. "Role of the Adhesion Molecule ICAM-1 (CD54) in Staphylococcal Enterotoxin-Mediated Cytotoxicity" *Eur. J. Immunol.*, 1991, pp. 131-135, vol. 21.

Fleisher, B. et al. "T-Lymphocyte Stimulation by Microbial Superantigens" *Chem. Immunol.*, 1992, pp. 36-64, vol. 55.

Fraser, James D. et al. "CD28 and T Cell Antigen Receptor Signal Transduction Coordinately Regulate Interleukin 2 Gene Expression in Response to Superantigen Stimulation" *J. Ex. Med.*, 1992, pp. 1131-1134, vol. 175.

Gilboa, Eli et al. "Immunotherapy of Cancer With Dendritic-Cell-Based Vaccines" *Cancer Immunol Immunother*, 1998, pp. 82-87, vol. 46, No. 2.

Hartwig, Udo F. et al. "Mutations Affecting MHC Class II Binding of the Superantigen Streptococcal Erythrogenic Toxin A" *International Immunology*, 1993, pp. 869-875, vol. 5, No. 8.

Herman, Andrew et al. "Identification of the Staphylococcal Enterotoxin A Superantigen Binding Site in the β1 Domain of the Human Histocompatibility Antigen HLA-DR", *Proc. Natl. Acad. Sci. USA*, 1991, pp. 9954-9958, vol. 88.

Hermann, Thomas et al. "Staphylococcal Enterotoxin-Dependent Lysis of MHC Class II Negative Target Cells by Cytolytic T Lymphocytes", *J. Immunol.*, 1991, pp. 2504-2512, vol. 146.

Hock, Randy A. et al. "Murine Neuroblastoma Vaccines Produced by Retroviral Transfer of MHC Class II Genes", *Cancer Gene Therapy*, 1996, pp. 314-320, vol. 3, No. 5.

Johnson, Howard M. et al. "Superantigens in Human Disease", *Scientific American*, 1992, pp. 92-111.

Karp, David R. et al. "The α1 Domain of the HLA-DR Molecule is Essential for High-Affinity Binding of the Toxic Shock Syndrome Toxin-1", *Nature*, 1990, pp. 474-476, vol. 346.

Menard, S. et al. "Mycobacterium Tuberculosis Gene Transfer in Melanoma Cells Induces Antitumoral Immunity in Mice" *Cancer Gene Therapy*, 1995, p. 318, vol. 2, No. 4.

Mayordoma, J.I. et al. "Bone Marrow-Derived Dendritic Cells Pulsed With Synthetic Tumour Peptides Elicit Protective and Therapeutic Antitumour Immunity", *Nature Medicine*, 1995, pp. 1297-1302, vol. 1, No. 12.

Mollick, Joseph A. et al. "Staphylococcal Exotoxin Activation of T Cells", *J. Immunology*, 1991, pp. 463-468, vol. 146.

Panina-Bordignon, Paola et al. "Identification of HLA-DRα Chain Residues Critical for Binding of the Toxic Shock Syndrome Toxin Superantigen", *J. Exp. Med.*, 1992, pp. 1779-1784, vol. 176.

Rust, Chantal, J.J. et al. "Specific Recognition of Staphylococcal Enterotoxin A by Human T Cells Bearing Receptors With the Vγ9 Region", *Nature*, pp. 572-574, vol. 346.

Webb, Susan R. et al. "T-cell Activation by Superantigens", *Curr Opinion in Immun.*, 1994, pp. 467-475, vol. 6.

Tomai, M. et al. "Superantigenicity of Streptococcal M Protein", *J. Exp. Med.*, 1990, pp. 359-362, vol. 172.

Fleischer, B. et al. "Superantigens and Pseudosuperantigens of Gram-Positive Cocci", *Med. Microbiol. Immumol.*, 1995, pp. 1-8, vol. 184.

Degnan, B. et al. "*Streptococcus pyogenes* Type 5 M Protein is an Antigen, Not a Superantigen, for Human T Cells", *Human Immunology*, 1997, pp. 206-215, vol. 53.

Esaki, Y. et al. "Role of Human Major Histocompatibility Complex DQ Molecules in Superantigenicity of Streptococcus-Derived Protein", *Infection and Immunity*, 1994, pp. 1228-1235, vol. 62, No. 4.

Anderson, W.F. "Human Gene Therapy", *Nature*, 1998, pp. 25-30, vol. 392(Supp.).

Verma, I. M. et al. "Gene Therapy—Promises, Problems and Prospects", *Nature*, 1997, pp. 239-242, vol. 389.

Gomez-Navarro, J. et al. "Gene Therapy for Cancer", *Eur. J. Cancer*, 1999, pp. 867-885, vol. 35, No. 6.

Ngo, J. T. et al. "Computational Complexity, Protein Structure Prediction, and the Levinthal Paradox", *The Protein Folding Problem and Tertiary Structure Prediction*, 1994, pp. 433 and 492-495, Merz (ed.) Birkhauser, Boston, MA.

Chiu, T-L. et al. "Optimizing Energy Potentials for Success in Protein Tertiary Structure Prediction", *Folding & Design*, May 1998, pp. 223-228, vol. 3.

Orkin, S. H. et al. "Report and Recommendations of the Panel to Assess the NIH Investment in Research on Gene Therapy", Dec. 1995, pp. 1-41.

Ross, G. et al. "Gene Therapy in the United States: A Five Year Status Report", *Human Gene Therapy*, Sep. 1996, pp. 1781-1790, vol. 7.

Ostrand-Rosenberg, S. et al. "Tumor-Specific Immunity Can Be Enhanced by Transfection of Tumor Cells with Syngeneic MHC-Class-II Genes or Allogeneic MHC-Class-I Genes", *Int. J. Cancer*, 1991, pp. 61-68, vol. 6.

Kalland, T. et al. "Targeting of Superantigens", *Cell Biophysics*, 1993, pp. 147-164, vol. 22.

Coupar, B. E. H. et al. "A General Method for the Construction of Recombinant Vaccinia Viruses Expressing Multiple Foreign Genes", *Gene*, 1988, pp. 1-10, vol. 68.

Eck, S. L. et al. "Scope of Gene Therapy", *Gene-Based Therapy*, pp. 77-101, Chapter 5.

Marshall, E. "Gene Therapy's Growing Pains", *Science*, Aug. 1995, pp. 1050-1055, vol. 269.

Hollingshead, S. K. et al. "Molecular Evolution of a Multigene Family in Group A Streptococci", *Mol. Biol. Evol.*, 1994, pp. 208-219, vol. 11, No. 2.

Hollingshead, S. K. et al. "Structural Heterogeneity of the Emm Gene Cluster in Group A Streptococci", *Mol. Microbiol.*, May 1993, pp. 707-717, vol. 8, No. 4.

Ji, Y. et al. "Intranasal Immunization with C5a Peptidase Prevents Nasopharyngeal Colonization of Mice by the Group A *Streptococcus*", *Infection and Immunity*, Jun. 1997, pp. 2080-2087, vol. 65, No. 6.

Bessen, D. et al. "Passive Acquired Mucosal Immunity to Group A Streptococci by Secretory Immunoglobulin A", *J. Exp. Med.*, Jun. 1988, pp. 1945-1950, vol. 167, No. 6.

Carbone, M. et al. "Multistep and multifactorial carcinogenesis: when does a contributing factor become a carcinogen?" *Seminars in Cancer Biol.*, Dec. 2004, pp. 399-405, vol. 14, No. 6.

Keith, C.T. et al. "Multicompenent therapeutics for networked systems", *Nat. Rev. Drug Discovery*, Jan. 2005, pp. 1-8, vol. 4, No. 1.

Tomai, M. et al. "Superantigenicity of Strptoccoccal M protein", *The Journal of Experimental Medicine*, 1990, pp. 359-362, vol. 172.

Lawman, M.J. et al. "ImmuneFX™: A Novel Immunotherapeutic Cancer Vaccine", *J. Immunotherapy*, 2005, pp. 614-615, vol. 28, Abstract only.

Biochemistry: John Wiley and Sons, Section 6-3 Chemical Evaluation, 1990, pp. 126-128.

Van Dyke, T. et al. "Cancer Modeling in the Modern Era: Progress and Challenges", *Cell*, Jan. 25, 2002, pp. 135-144, vol. 108.

Yamaguchi, Y. et al. "Adoptive immunotherapy of cancer using activated autologous lymphocytes—current status and new strategies", *Human Cell*, Dec. 2003, pp. 183-189, vol. 16, No. 4.

Cranmer, L.D. et al. "Clinical applications of dendritic cell vaccination in the treatment of cancer", *Cancer Immunol. Immunother.*, Apr. 2004, pp. 275-306, vol. 53, No. 4.

Wallack, M.K. et al. "A Phase III randomized, double-blind multiinstitutional trial of vaccinia melanoma oncolysate-active specific immunotherapy for patients with stage II melanoma", *Cancer*, Jan. 1, 1995, pp. 34-42, vol. 75, No. 1.

Giantonio, B.J. et al. "Superantigen-based Immunotherapy: A Phase I Trial of PNU-214 A Monoclonal Antibody-Staphylococcal Enterotoxin A Recombinant Fusion Protein, In Advanced Pancreatic and Colorectal Cancer", *J. Clin. Oncol.*, May 1997, pp. 1994-2007, vol. 15, No. 5.

Lee, S.T. et al. "Therapeutic Vaccine for Lymphoma", *Yonsei Medical Journal*, 2007, pp. 1-10, vol. 48, No. 1.

Baskar, S. et al. "Autologous Lymphoma Vaccines Induce Human T Cell Responses Against Multiple, Unique Epitopes", *J. Clin. Invest*, May 2004, pp. 1498-1510, vol. 113, No. 10.

Chung, Y.S. at al. "An NKT-Mediated Autologous Vaccine Generates CD4-T Cell-Dependent Potent AntiLymphoma Immunity", *Blood*, Jun. 2007, pp. 2013-2019, vol. 110, No. 6.

* cited by examiner

TUMOR CELL VACCINES

CROSS-REFERENCE TO RELATED APPLICATIONS

This application is a continuation in part of U.S. application Ser. No. 10/964,471, filed Oct. 13, 2004, now issued as U.S. Pat. No. 7,348,015, which is a continuation in part of U.S. application Ser. No. 10/652,578, filed Aug. 29, 2003, now issued as U.S. Pat. No. 7,094,603, which is a continuation in part of U.S. application Ser. No. 09/950,374, filed Sep. 10, 2001, now abandoned, which is a continuation of U.S. application Ser. No. 09/394,226, filed Sep. 13, 1999, now abandoned, which is a continuation of International Application No. PCT/US99/00787, filed Jan. 14, 1999, which claims benefit of U.S. provisional application Ser. No. 60/071,497, filed Jan. 14, 1998.

BACKGROUND OF THE INVENTION

Cancer is the second most common disease and also one of the most feared. Cancer occurs when cells continue to divide and fail to die at the appropriate time. Under normal circumstances, the many types of cells that make up the body grow and divide to produce more cells as they are needed in order to maintain a healthy body. Tumors may form when this orderly process is disrupted by changes in genes that control normal cell growth and death and cellular growth becomes uncontrolled. Genetic changes that arise internally due to defective DNA repair or may be induced by external factors such as diet, exposure to ultraviolet or other types of ionizing radiation, viruses such as cervical papillomaviruses, exposure to chemical carcinogens in the workplace or in the environment, drug or tobacco use, or to agents such as asbestos. Some detrimental genetic alterations are inherited.

During the transformation process, malignant neoplasms grow into a disorganized mass, however, they usually retain some resemblance to the normal tissue from which they arise. Upon histological examination, tumors can be classified according to cell type origin. For example, tumors of epithelial origin are classed as carcinomas. Sarcomas arise from tissues of mesodermal origin. Carcinomas and sarcomas can be further distinguished as adenocarcinomas, hepatocarcinomas, osteosarcomas or fibrosarcomas. Other types of cancers include leukemias and various types of tumors of primitive origin such as neuroblastoma and meduloblastoma. Malignant cancers can affect humans as well as many animal species.

It is well understood that the main reason all cancer cells are not removed from the body is because these cells are seen by the immune system as "self"; i.e., they are the host's own cells, and because they are poorly immunogenic.

In order to develop immunotherapies for the treatment of cancer, the different ways parasitic tumor cells evade the immune system are taken into consideration, particularly in how these abnormal cells develop. Although each tumor is thought to begin by the clonal reproduction of a single cell, additional changes eventually give rise to a heterogeneous mixture of different subclones, which are in effect antigenic variants. Once under the selective pressure of the host's immune response, low antigenic variants gain advantage over subclones that express fewer or more immunogenic molecules. The less immunogenic and the lower the density of the tumor-associated antigens on the plasma membrane, the more likely the tumor cells will fall below the threshold of immune detection and become invisible to host surveillance.

Tumor antigens are subject to antigenic modulation, i.e., the tumor antigens appear to be temporarily lost after exposure to specific antibodies, although alternatively, tumors may simply suppress the activities of immune effector cells such as T-cells and macrophages. On the other hand, a few isolated tumor cells may contain too few antigens to stimulate an effective immune response so that by the time immunity has developed, the tumor is beyond the capability of the immune system to destroy it. Some tumors may even interfere with normal immune responses by invading lymphoid tissues or secreting immunosuppressive factors.

While tumor-specific protein or peptide vaccines are by definition specific for a particular tumor, a major concern in their use is tumor heterogeneity. Although tumor cell clones expressing the tumor-specific peptide epitopes may be destroyed, clones that do not express the epitope escape immune attack, due to the fact that tumors are not clonal but are comprised of a diversity of cells.

Conventional cancer treatments typically include some form of chemotherapy involving use of drugs that are cytotoxic to the cancer cells, but also tend to kill non-cancerous cells. One approach to lowering therapeutic drug toxicity is transfection of healthy, normal stem cells with transgenes that confer resistance to these agents. In theory, this results in cytotoxic drug-resistant cells and allows the administration of higher, therapeutically significant doses of chemotherapeutic agents. Use of transfected cells has been suggested for protection of bone marrow cells since bone marrow cells are rapidly dividing and thereby most at risk to chemotoxicity and in fact has shown some success in animal models, Licht et al., 2000.

However, use of gene therapy to modify normal cells appropriate for cancer treatment has several drawbacks although in vivo treatments for malignant melanoma in dogs, for example, has met with some success. A positive response to tumor regression was observed over a period of 6-12 weeks after a direct DNA injection encoding a *Staphylococcus* antigen and GM-CSF cytokine (W096/36366). Liposome/Staphylococcal antigen injections alone, however, failed to show any effect even after 17 weeks, suggesting that tumor regression was caused by a toxic effect generated by the cytokine or cytokine/antigen combination in the cancer cells.

Immunotherapy methods based on manipulation of the host immune system to identify cancer cells as non-self; i.e., methods to mobilize and strengthen the immune system so that it can selectively destroy and/or inhibit proliferation of cancerous cells, is gaining more attention. This is due to the recognition that the host itself may be able to generate the safest and most effective defense against cancer.

The vast majority of malignancies arise in immunocompetent hosts, raising doubts as to whether a general strengthening of the immune system can ever be effective in targeting cancer cells, which are not always recognized as foreign by the host. Tumor cells carry tumor-associated or tumor-specific antigens that are different from their normal counterparts. Tumor-associated antigens such as oncofetal antigens are normally synthesized during embryogenesis but are not found on adult cells, can be generated by the activation of normally repressed genes. Some antigens are present but masked; while others may be lost when the cells become transformed and thus alter the profile of adjacent molecules by their absence. Antigens may also be modifications of normal molecules or may be nuclear or cytoplasmic and thus hidden from immune surveillance. Tumor-specific antigens are restricted to tumor tissues. They are not found in normal adult or fetal tissues and are rare.

Antigens, bacterial and viral, have been used in combination with cytokine or other immunomodulator genes delivered by means of adenovirus, retrovirus or plasmid vectors (WO 94/21808; WO 96/29093). The presence of cytokines may contribute to limited success of some of these approaches. In certain cases, a highly destructive and specific response to otherwise nonimmunogenic tumors can be elicited by the insertion of genes encoding interleukin-2, interleukin-4, interleukin-12, interferon-$\gamma$, interferon-$\alpha$ and/or tumor necrosis factor into the tumor cells as well as into cytotoxic lymphocytes or macrophages, although serious side-effects may occur at high doses.

Oncophages have been used to lyse autologous tumor cells in the hope of generating a tumor-specific response. Others have transfected tumor cells with immunotoxins (Wallack, et al., 1995). Patients also have been vaccinated with specific tumor antigens, tumor-specific monoclonal antibodies, HSP 70 purified from autologous tumor cells, autologous T cells activated against tumor cells ex vivo. These methods focus on specific aspects of the immune response to particular tumor characteristics.

Autologous tumor-infiltrating lymphocytes have been used in genetic immunomodulation studies because of their inherent specificity for the tumor and their ability to home back to the tumor site when reinfused into the patient. Normal tissue has been protected by stably transfecting normal bone marrow cells with cytokine genes prior to chemotherapy, thereby achieving a more continuous effect while obviating the need to infuse drugs which have short half-lives and produce systemic side effects when delivered intravenously (Yamaguchi, et al., 2003).

An immunostimulating vaccine has been described in U.S. patent Ser. No. 10/964,471 where autologous tumor cells were engineered to express a priming antigen, Emm55 and used to formulate a vaccine. Extensive in vivo tests in a murine model demonstrated protection from a highly invasive neuroblastoma tumor and an inhibitory/therapeutic effect when administered after tumors had developed.

There are currently just over 100 cancer vaccines in the developmental pipeline for use in humans. Collectively, they employ a diverse array of technology platforms with approximately 66% being antigen-specific, 21% being polyvalent and 14% being dendritic cell vaccines. Despite the intense interest in antigen-specific vaccines, the cell-based therapies have demonstrated the most compelling clinical data. In addition to the obvious human medical markets, there is an analogous and equally expanding veterinary cancer market for companion animals.

Both pharmaceutical and biotechnology companies are turning to the companion animal healthcare market which is currently valued in the billions of dollars and is growing at a rate of 10% per year. This market growth is in response to pet owners who are demanding better care and access to cutting-edge technology for their animals. Although the pet population has increased somewhat, the key driver for growth is the willingness of pet owners to spend and the ability of veterinarians to meet the demand. In the US alone, pet owners spend over $19 B a year on veterinary care, which is increasingly shifting to veterinary specialists including oncologists, ophthalmologists and orthopediatricians, and other specialists. For many companion animal cancers, systemic chemotherapy is the current treatment of choice even though recurrence and multi-drug resistance are common. In addition, chemotherapy is administered only as a palliative therapy, to improve and prolong life, and the pet owner is often reluctant to treat with chemotherapy because these toxic chemical commonly cause side effects such as anorexia, vomiting, diarrhea, sepsis and even death and can cost up to $5,000 over a 6 month period.

In the veterinary market, it has been estimated that 45% of dogs 10 years or older will die of cancer, and this number is increasing at a rate of 38% per year in some states. While lymphoma is not breed-specific, an example of the incidence of lymphoma in Golden Retrievers (60,000 per year, which is 1 in 8) provides an indication of the nature of the market for this type of cancer. Each year, there are approximately 10,000 new cases of osteosarcoma in dogs and cancer accounts for 60% of all Golden Retriever deaths. The total canine cancer market in the US alone can be conservatively calculated by assuming a 0.3% incidence of cancer in the US population of 64,000,000 pet dogs. Estimates for the US canine oncology market are approximately $192 M. Estimates for the development of animal immunotherapeutic treatments for all companion animals, including cats, horses and birds as well as dogs, represents a market opportunity for annual revenues of $3 B.

BRIEF SUMMARY OF THE INVENTION

The present invention is related to the development of a highly effective in vivo lymphoma vaccine. The vaccine was prepared from lymphoma cells engineered to express an Em55 antigen which induced tumor-protective immunity. The modified cancer cells are highly immunogenic to the host, yet show no toxic side effects. The vaccine produces a tumor-specific immune response in canine models of disease.

Effective anti-tumor immunity does not occur to any significant level in most advanced-stage disease. This failure of the host to raise an immune defense is attributable to insufficient and/or ineffective immune stimulation. Normally, activation of the immune response is triggered by activating dedicated antigen-presenting cells that in turn are activated by the presence of foreign antigens. The stimulation of antigen presenting cells induces an orchestrated series of events involving natural killer cells, T helper and cytotoxic T cells, macrophages, and B cells, as well as the production and secretion of multiple cytokines, antibodies, chemokines and colony stimulating factors.

The cell vaccine of the present invention maximizes the potential of the initiator of the immune cascade, the "foreign" antigen. Rather than depend on tumor-associated and/or tumor-specific antigens to act as the initiator or priming antigen, a priming antigen is supplied, the cascade is initiated and the immune response to the antigens associated with the tumor is amplified accordingly. This amplifies the normal host immune mechanisms in vivo because the engineered cancer cells prime a strong response and deliver the molecules that define the specificity. The vaccine cells are engineered from autologous or allogeneic cancer cells obtained from cell lines or tissue. An immune response is generated to the specific cancer without toxicity to normal cells. The treatment is not only selective but also shows long-term results in the animal models.

The present invention shows that the highly immunogenic priming antigen Emm55 can be expressed in targeted tumor cells. The modified cells can be used to treat oncological diseases in mammals, including dogs, cats, horses, animals of agricultural significance such as cows, sheep chickens and turkeys and humans. In particular, modified lymphoma cells are shown to significantly increase life span in dogs with up to Stage V lymphomas.

In preparing the Emm55 cell vaccine, a polynucleotide coding for the highly immunogenic priming antigen, Emm55 is introduced into a lymphoma or lymphoma cell so that the antigen is expressed by the transformed cells. While demonstrated with this cell type, other cancer cell types can be similarly engineered, including leukemias, lymphomas and their various metastases and micro metastases.

The disclosed methods are surprisingly effective for treating well-established solid tumors; i.e., the lymphomas in the canine models tested. The canine models used are particularly relevant to human cancers because they are accepted models for non-Hodgkin's lymphoma in humans. The anatomy of the dog is more similar to humans than is the rodent anatomy. Naturally occurring cancers have very similar etiologies in dogs and humans and treatments that are successful in treating a disease in humans tend to work well in treating the same disease in dogs; in fact, canine lymphoma is a well accepted model for non-Hodgkin's lymphoma in humans.

The invention is also applicable to methods for treating or preventing lymphomas and other oncological diseases in humans. The method comprises modifying a cell to express a highly immunogenic antigen in a cell, and may optionally include further modifying the cell to express a second antigenic polypeptide before administering the transformed cells. In one embodiment, the method comprises expressing an immunogenic antigen such as Emm55 or a functional variant thereof and, optionally, a cytokine on a cell surface and providing the subject with the transformed cells that express the antigen and the cytokine.

While the invention is illustrated with Emm55 (also known as EmmL 55), other immunogenic proteins can be expressed in a selected cancer cell to provide a useful vaccine. The protein EmmL 55, or Emm55, as discussed, has been employed to modify a neuroblastoma tumor cell. The resulting Emm55 cancer cell vaccine was effective prophylactically and therapeutically in murine models. In contrast to some so-called superantigens, Emm55 does not produce an overblown immune response in a non-immune fashion so that the immune response to Emm55 does not result in clearance of the immune effectors before a therapeutic effect is realized. Thus, selection of an appropriate priming antigen includes consideration of whether or not too strong an immunological response will be generated.

A number of other priming antigens can be used, and are first identified as "priming" antigens, then selected on the basis of availability of the encoding gene. The emm55 gene for example is readily available; however, other foreign genes such as MHC genes, such as MHC class I, II and DR genes, and/or genes encoding cytokines can be inserted and expressed in the cell transformed to express the antigen and optionally used in combination with each other. Particularly highly immunogenic streptococcal antigens include those from groups A, D and B. Other immunogenic antigens may also be employed, including staphylococcal endotoxins B, C1, C2, C3, D, E, F, *Mycoplasma arthriditis* toxins, *Shigella* toxins, *Pseudomonas diphtheria* antigens and mouse mammary tumor MTV-7 toxin.

The invention also includes truncated immunogenic proteins, and in particular the polynucleotides that encode truncated proteins that exhibit higher activities or higher cell-surface expression compared to the full-length parent polypeptide when expressed in transformed cells.

Tumor cells expressing a priming antigen can be irradiated prior to administration. While boiling and freeze-thaw loading techniques fail to generate protective immunity, irradiated cells seem to retain immunogenicity (Soiffer et al, 1998). Irradiation produces cells that are viable but unable to replicate.

Selected cancer cells can be transformed in vivo, however, in order to be effective it is believed that specific targeting modes would have to be associated with the transforming or infecting means. In vivo transformations can be accomplished using any of a variety of methods well-known in the art, such as using targeted liposomes, viral vectors, and direct injection with naked DNA via numerous methods, but it is believed that ex vivo methods may be more effective for non-solid tumors like leukemias while in vivo methods may be preferable for solid tumors.

Any cancer cell may be used with the disclosed method. Sources include the host or other mammalian sources. The cells can be modified with polynucleotide molecules encoding highly immunogenic antigens (e.g., Staphylococcal or Streptococcal), foreign MHC antigens and/or cytokines using standard techniques known in the art. Cells are preferably transformed ex vivo for in vivo use. When cancer cells are modified ex vivo, according to the invention, they can be reinfused into the mammal.

Encoding polynucleotides can be delivered to the cells using, for example, targeted liposomes that harbor the polynucleotide molecules. Viral vectors, such as adenovirus, adeno-associated virus, retrovirus, pox virus, herpes virus, plasmids and nucleic acid, can also he used for transforming cells with the polynucleotide molecules encoding the selected highly antigenic polypeptides useful in the practice of the present invention. Cells can also be transfected using naked DNA, e.g., transfection by direct injection of a tumor with naked DNA encoding proteins useful in the subject methods.

The present invention demonstrates that the disclosed cancer cell vaccine is useful as a therapeutic. Immunogenic compositions, useful as vaccines, may be prepared most readily from immunogenic peptides and a select cancer cell. The cancer cell will be from host cancer cells or from the same type of cancer cells, which may be obtained from appropriate cell lines or from non-autologous tumor cells. Ideally, the cancer cells are taken from the host; however, cancer cell vaccines can still be employed when autologous cells cannot be obtained. In such a case, vaccines prepared from cell lines or nonautologous donors can be administered.

Oncological disorders that can be treated using the methods and compositions of the present invention include not only lymphomas, sarcomas and leukemias, but also carcinomas of the bladder, breast, lung, cervix, colon, kidney, liver, ovary, prostate, pancreas, cartilage, testis, tongue, uterus and thyroid; sarcomas such as those of the pelvis, rhabdomyo (muscle), bone and osteogenic, brain tumors; gliomas; gliobastomas; neuroblastomas; melanoma; hepatomas; medulloblastoma; and Wilm's Tumors and circulating tumor cells for each of these cancers.

The amino acid sequences of the proteins of the subject invention can be prepared from nucleotide sequences other than the wild-type or native sequences. Functionally equivalent nucleotide sequences encoding the amino acid sequence of these proteins and fragments thereof can be prepared by known synthetic procedures. As is well known in the art, the amino acid sequence of a protein is determined by the nucleotide sequence of the DNA. Because of the redundancy of the genetic code, a single amino acid can be coded for by more than one coding nucleotide triplet (codon). Accordingly, different nucleotide sequences can code for a particular amino acid sequence. Accordingly, the invention includes use of such functionally equivalent nucleotide sequences having substantially the same antigenic, immunogenic, or therapeutic activity.

BRIEF DESCRIPTION OF THE DRAWINGS

FIG. 4 shows cell mediated response in individual dogs at day 0, 21 and 28. The data indicate that subjects receiving autologous vaccine produced a strong cellular response to their own tumor cells and that the response increased over time.

BRIEF DESCRIPTION OF THE SEQUENCES

Figure 1:
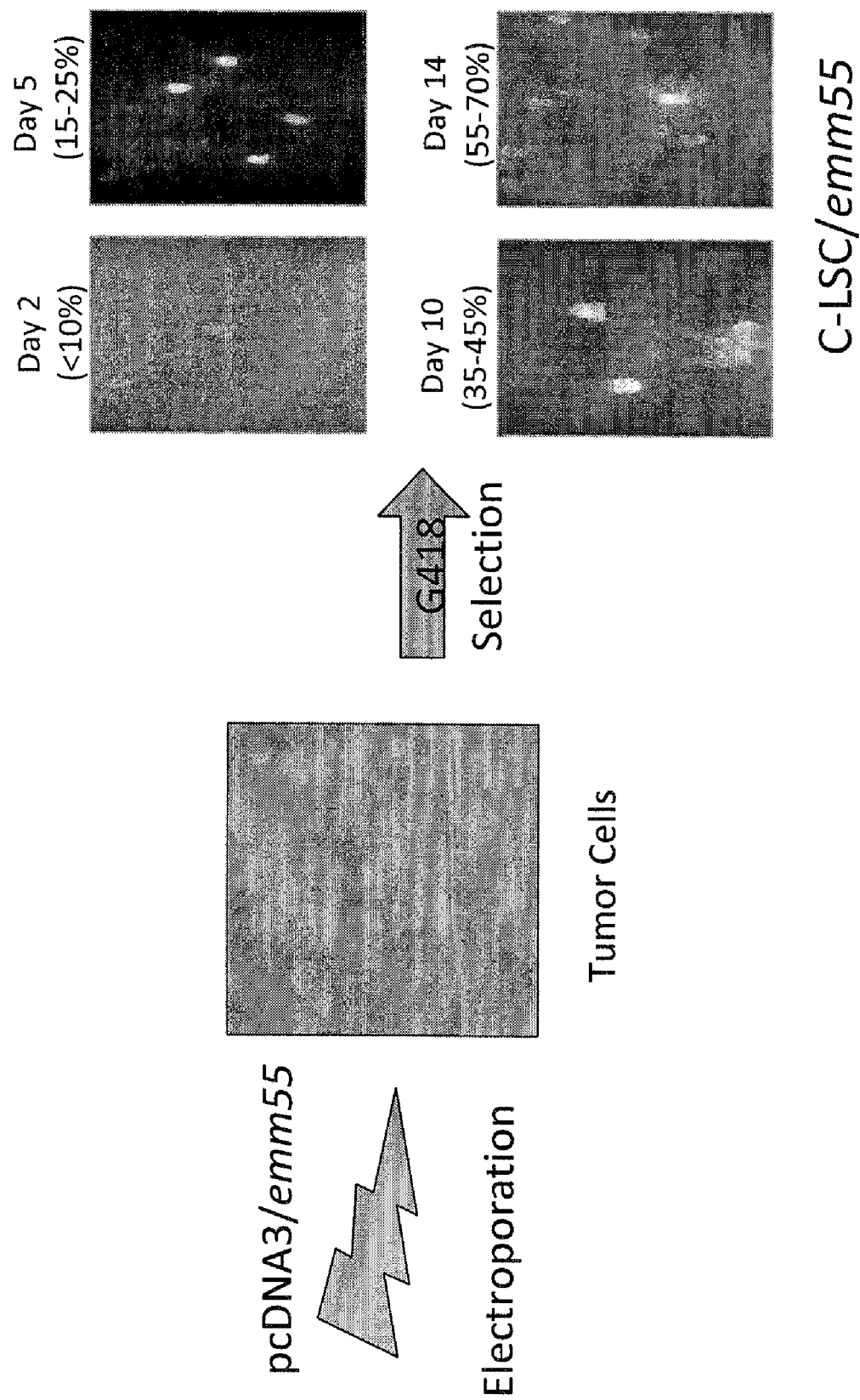
FIG. 1 shows the subcloning of the emm55 gene into the pcDNA3 expression vector using standard recombinant DNA methods (pcDNA3/emm55). Lymphoma cells were transfected with the pcDNA3/emm55 plasmid via electroporation and Emm55-expressing cells were selected in the presence of G418 to produce the autologous vaccine. Autologous C-LSC/emm55 cells were used for all subsequent experiments.

SEQ ID NO: 1 is from the T7 promoter of the emm55 gene insert in pcDNA3/emm55. The sequence of the emm55 gene insert was experimentally determined from the 5' end of the polynucleotide using primers homologous to the T7 promoter region of the pcDNA3 multiple cloning region.

SEQ ID NO:2 is from the SP6 promoter of the emm55 gene insert in pcDNA3/emm55. The sequence of the emm55 gene insert was experimentally determined from the 3' end of the polynucleotide using primers homologous to the SP6 promoter region of the pcDNA3 multiple cloning region is shown.

DETAILED DESCRIPTION OF THE INVENTION

Cancer vaccines and other immunotherapies function by activating the immune system to fight tumors in either a specific or non-specific manner. While the mechanism of action differs with different types of therapy, the ultimate goal is the same, i.e. to turn the immune system against the tumor cells it would otherwise tolerate. An optimum strategy is to design an immunotherapy in which the tumor cells are made to appear "foreign" to the immune system so that they are recognized as dangerous and as such can be eradicated with the full force of both arms of the immune response.

The described cancer vaccine is based on engineering tumor cells to appear foreign to the immune system. The vaccine acts by placing a "foreign" or priming antigen on the surface of the autologous tumor cells. The priming antigen, Emm55, which is a serotyping protein normally expressed on the surface of the bacterium, *Streptococcus pyogenes*, is supplied to the tumor cells in genetic form as a DNA plasmid. Recognition of the priming antigen initiates a tumor-specific immune response.

Clinical evaluation of a cancer cell vaccine such as the Emm55 vaccine, is important for several reasons: 1) the bacterial antigen, Emm55, is a highly antigenic protein; 2) Emm55 is a common antigen and reintroduction is expected to elicit a rapid and increased anamnestic response, which in turn will lead to a significant additional therapeutic effect; 3) Emm55 is one of a very few bacterial antigens to have been successfully expressed on the surface of mammalian cells; 4) Emm55 induces no toxic effects in model in vivo studies and showed 88% long-term survival in a murine neuroblastoma model relevant to human disease; 5) effects of the vaccine are dose-dependent and evoke both humoral and cellular immune responses; and 6) the cancer cell vaccine approach is simple, straightforward, non-toxic and patient-friendly and potentially useful with virtually any type of cancer.

Lymphoma is the third most common cancer diagnosed in dogs and is a cancer of either B or T lymphocytes. Although any age dog can be affected, the average age of dogs with lymphoma is between 6-9 years. Breeds such as Boxers, German Shepherds, Golden Retrievers, Scotties and Pointers are more likely to develop this type of cancer, yet males and females are equally at risk.

As described herein, an Emm55 cell vaccine was tested in dogs diagnosed with lymphoma. Canine lymphoma is a well-excepted model for non-Hodgkin's lymphoma in humans and is a common, spontaneously occurring hematological form of cancer in dogs. The annual incidence of these highly aggressive tumors has been estimated at a rate of 33 per 100,000 dogs.

The examples provided herein demonstrate the safety and tolerability of the Emm55 lymphoma cell vaccine and provide evidence that the vaccine initiates a tumor-specific immune response in dogs with canine lymphoma. The vaccine elicits a tumor-specific immune response (both humoral and cell-mediated) in all the canine subjects with lymphoma and produces no toxic side effects.

Success in using a cellular vaccine has previously been demonstrated in a murine model system (U.S. publication number 2005-0106130 A1, May 19, 2005). Expression of a highly immunogenic (priming) antigen in a neuroblastoma cell prevented or drastically reduced tumor development with no observable metastasis in mice. Of 72 mice inoculated with tumor cells that expressed the priming antigen, only two developed tumors, and after several days, these tumors regressed completely. This was in contrast to 67 of the 72 mice inoculated with unmodified tumor cells, which developed tumors.

The observation that mice inoculated with tumor cells expressing the priming antigen were protected from challenge with unmodified tumor cells was also demonstrated. The priming antigen initiated an increased immune response specific to the neuroblastoma cells as evidenced by the presence of anti-tumor cell antibodies in the sera of individual mice.

Neuroblastoma was a convenient choice as a preliminary test cancer because the well-established mouse cancer cell, Neuro-2a, was recognized as mimicking the disease in humans. It is an especially aggressive tumor that can develop from small numbers of cells and will consistently kill its host within 2 weeks of onset if left untreated. The aggressive characteristics of Neuro-2a in S/J mice make any improvement in its prognosis highly significant. Another characteristic of this model is that Neuro-2a grows as a heterogeneous population of cells, a characteristic it shares with human neuroblastoma tumors. The results in the murine model suggested parallel results in humans for aggressive tumors such as neuroblastomas.

However, the results with mice injected with neuroblastoma cells did not provide an expectation of viable treatment modalities for naturally-established tumors in other classes. The in vivo response with the neuroblastoma system was elicited because the modified cancer cells were recognized as foreign or non-self. There was no assurance of success with already established lymphomas. As demonstrated herein, the response seen in the canine models was unexpectedly positive.

Regardless of whether the cancer is a leukemia, a lymphoma, a sarcoma, a carcinoma or any other type of malignancy, because cancers are made up of cells and are amenable through genetic modification to expressing the priming antigen, this demonstration in an established lymphoma provides an expectation that any type of cancer will be amenable to participating in the development of its own vaccine.

The cancer cell vaccine of the present invention can be prepared ex vivo by transforming representative cells of the lymphoma with an Emm55 gene (SEQ ID NO:1). Transformation methods are well-known and can be used to insert an appropriate expression vector into a cell; e.g., by transfection, infection or electroporation. However, for in vivo administration, a preferred formulation comprises an expression vector, which contains the gene encoding the priming antigen. This type of formulation can be directly introduced into the tumor via needle and syringe, gold particles using ballistic guns (gene guns), liposomes or by jet injection techniques.

Once formulated, the cancer cell vaccines are typically prepared as injectables in the form of suspensions. The cell suspensions may be mixed with excipients which are pharmaceutically acceptable and compatible with the cells. Suitable excipients include, for example, water, saline, dextrose, glycerol, ethanol or the like and combinations thereof. In addition, if desired, the vaccine may contain minor amounts of auxiliary substances such as wetting or emulsifying agents, pH buffering agents, or adjuvants that enhance the effectiveness of the vaccine.

The vaccines are conventionally administered parenterally, by injection, for example, either subcutaneously or intramuscularly and are administered in a manner compatible with the dosage formulation, and in such amount as will be therapeutically effective and immunogenic. Alternatively, intradermal injection of the vaccine may be preferable. The quantity to be administered depends on the subject to be treated, including, e.g., the capacity of the host's immune system to synthesize antibodies, and the degree of protection desired. Precise amounts of the transformed cells required will depend to some extent on the judgment of the practitioner and the age, health, sex, etc., of the host. However, suitable dose ranges may be determined from animal models and initial clinical studies. Generally, it is contemplated that on the order of $10^6$ transformed cells will be required.

Adjuvants may be required in cases where the host immune system is weakened or compromised. Adjuvants commonly used include agents such as aluminum hydroxide or phosphate (alum), admixture with synthetic polymers of sugars (Carbopol®), aggregation of protein in the vaccine by heat treatment (e.g. 70-101° C.) Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable vegetable oils vehicles such as mannide mono-oleate (Aracel A) or emulsion with a 20% solution of perfluorocarbon (FLUOSOLDA®) used as a block substitute may also be employed.

In certain instances, it will be desirable to administer multiple doses of the vaccine, usually not exceeding six vaccinations, more usually not exceeding four and preferably one or more, usually two or three. The vaccinations will normally be at from two to twelve week intervals, more usually from three to five weeks. Periodic boosters at intervals of 1-5 years, usually three years, may be required to maintain a protective level of antibodies and memory T cells.

Pharmaceutical Compositions

Pharmaceutical compositions containing the cancer cell vaccine are preferably administered parenterally, intraperitoneally, intradermally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Upon formulation, solutions will be administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intradermal and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Materials and Methods

The immunotherapy described in the methods herein is based on the introduction of a bacterial gene encoding Emm55, which is a serotyping protein normally expressed on the surface of *Streptococcus pyogenes*, into autologous tumor cells. The strong tumor-specific immune response initiated by this vaccine in pre-clinical studies resulted in an 88% long-term survival rate in mice which would have otherwise succumbed within a matter of weeks.

Canine lymphoma is a highly aggressive hematological tumor and is one of the most common forms of cancer in dogs. The annual incidence rate is 33 in 100,000 dogs. Chemotherapy is the current treatment of choice; however, recurrence and multi-drug resistance are common. While dogs of all breeds recently diagnosed with lymphoma were eligible for the study, they must not have received prior chemotherapy or radiation therapy and owners must have enrolled their pets in the study and agreed to comply with trial policies.

All animal care, including the administration of the experimental cell therapy, was carried out at Florida Veterinary Specialists and Cancer Treatment Center. Because diagnosis usually occurs late in the development of lymphoma, the dogs on the trial had advanced stage disease (stage 4/5) with a life expectancy of between 2 to 8 weeks.

The achievement of the two endpoints of this successful trial provides support for use of similarly designed cell therapies for use in humans for Non-Hodgkin's lymphoma as well as other tumor types associated with cancers in defined locations.

Canines

The dogs participating in this study had advanced stage disease with a life expectancy of 2-8 weeks. Of the 9 dogs recruited for the study, 2 were withdrawn for reasons unrelated to the study. Earlier stage animals are not generally diagnosed until late in the development of lymphoma and no animals in this study were diagnosed below Stage IV. Table 1 lists the criteria for identification of the clinical staging of the lymphoma.

TABLE 1

| Stage | Definition |
| --- | --- |
| Stage I | Involvement of a solitary lymph node or lymphoid tissue in a single organ (i.e. nasal cavity) |
| Stage II | Regional involvement of multiple lymph nodes |
| Stage III | Generalized lymph node enlargement |
| Stage IV | Involvement of liver and/or spleen |
| Stage V | Involvement of bone marrow (some classifications consider cutaneous involvement in this stage) |
| Substage a | Without systemic signs of disease (patient generally has no symptoms) |
| Substage b | With systemic signs of disease (patient does not feel well) |

The 7 dogs in the study were both male (5) and female (2) of various breeds; Bulldog, Vizsla, Greyhound, Golden Retriever, Dachshund, Corgi and Chow and their ages ranged from 4 to 11 years (Table 2). Autologous vaccine was produced for each dog from biopsies taken from regional lymph nodes. Animals were vaccinated approximately 2 weeks from the time of biopsy. The intravenous dose, $1 \times 10^7$ irradiated cells, was the same for all dogs. Each dog received weekly vaccine inoculations for a total of 4 weeks and in most cases went on to receive monthly doses.

Table 2 shows Emm55 cell vaccine induced cross reactive humoral responses for canine lymphocytes. The data are from Western Blot and densitometry analysis showing the degree of cross reactivity between immune sera from vaccinated dogs with tumor cells from other breeds.

TABLE 2

| Target cell origin | Vizsla | Grey-hound | Golden Retriever | Dachshund | Bull-dog | Chow |
| --- | --- | --- | --- | --- | --- | --- |
| Visla | 4+ | 3+ | 4+ | 3+ | 3+ | 3+ |
| Greyhound | 3+ | 4+ | 3+ | 4+ | 3+ | 4+ |
| Golden. Retriever | 3+ | 3+ | 4+ | 3+ | 3+ | 3+ |
| Dachshund | 3+ | 4+ | 3+ | 4+ | 4+ | 3+ |
| Bulldog | 4+ | 3+ | 3+ | 3+ | 4+ | 4+ |
| Chow | 3+ | 3+ | 3+ | 4+ | 3+ | 4+ |

Following are examples that illustrate representative materials and procedures for practicing the invention. These examples are intended for illustrative purposes only and should not be construed as limiting.

EXAMPLE 1

Vaccine Preparation

Autologous tumor cells were isolated from tumor biopsies, transfected by electroporation with a plasmid vector containing the emm55 gene, selected on G418, expanded, γ-irradiated and reintroduced by intravenous injection at a cell concentration of $3\times10^7$ per vaccine dose. FIG. 1 shows the cell vaccine development strategy. The emm55 gene was subcloned into the pcDNA3 expression vector using standard recombinant DNA methods (pcDNA3/Emm55). The polynucleotide fragment containing the emm55 gene was excised from the plasmid, pJL1A602, using the restriction enzymes, Bam HI and EcoRI and subcloned into the multiple cloning site of the pcDNA3 plasmid expression vector which had been restricted with the same enzymes. The resultant plasmid DNA construct was designated, pcDNA3/emm55.

Canine lymphoma cells were transfected with the pcDNA3/Emm55 plasmid via electroporation, and Emm55-expressing cells were selected in the presence of G418 (C-LSC/Emm55) to produce the autologous ImmuneFx vaccine. To date, tumor cells from 14 out of 14 primary canine lymphoma biopsies have been successfully transfected to produce the vaccine.

Three doses of vaccine were given at 1 week intervals. The dogs were monitored for 24 hr post inoculation for adverse reactions. Sera and lymphocytes were collected at the time of each vaccination.

Figure 2:
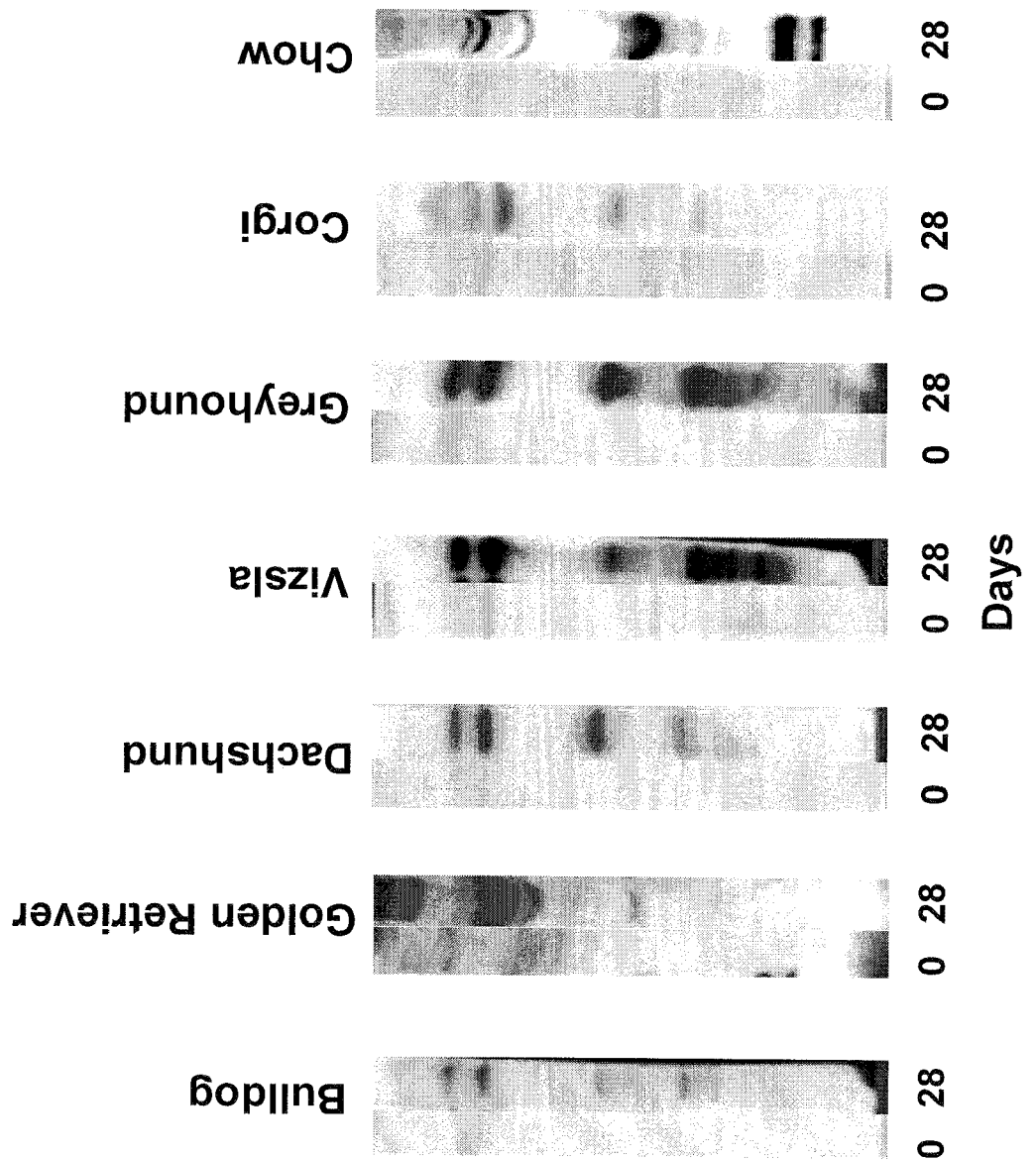
FIG. 2 is a Western Blot analysis of pre-immune sera (day 0) and post-immune sera (day 28) from subjects receiving the autologous cancer vaccine, showing that all dogs had strong reactivity to multiple tumor-specific antigens.
Figure 3:
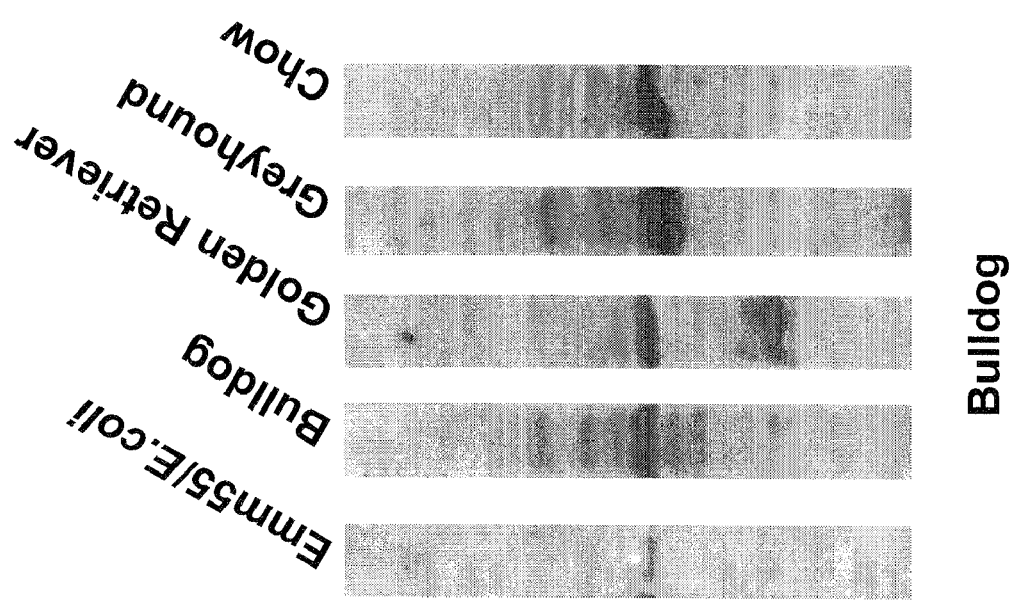
FIG. 3 is a Western Blot analysis of immune sera from a Bulldog, showing cross reactivity of the humoral response to tumor cells from several other breeds.
Figure 4A:
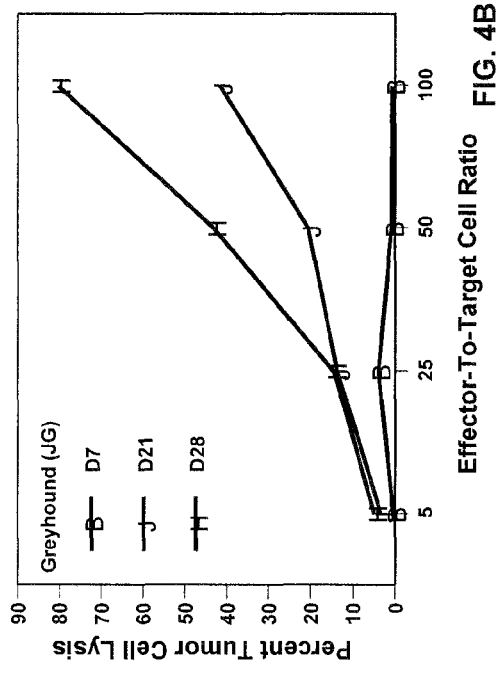
FIG. 4A shows cell mediated response in a Vizsla.
Figure 4B:
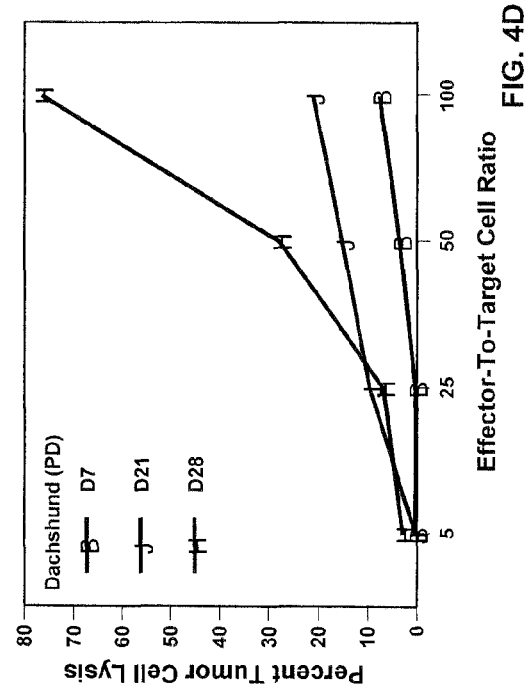
FIG. 4B shows cell mediated response in a Greyhound.
Figure 4C:
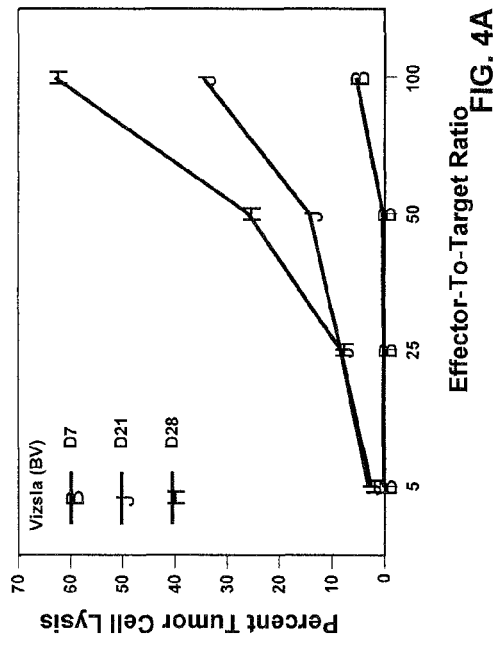
FIG. 4C shows cell mediated response in a Golden Retriever.
Figure 4D:
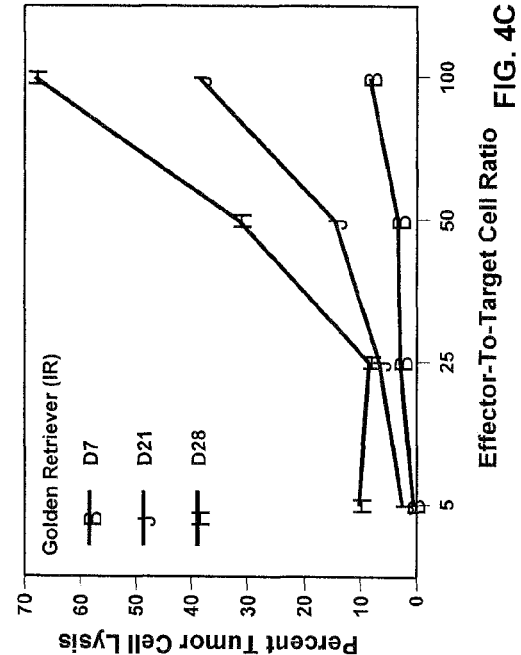
FIG. 4D shows cell mediated response in a Dachshund.
Figure 4E:
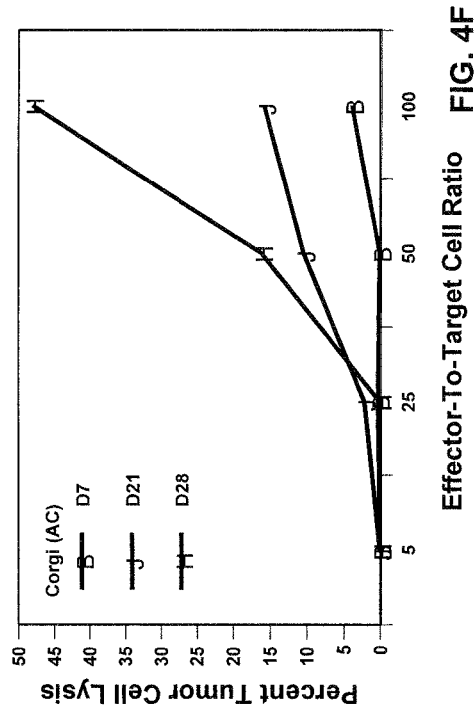
FIG. 4E shows cell mediated response in a Bulldog.
Figure 4F:
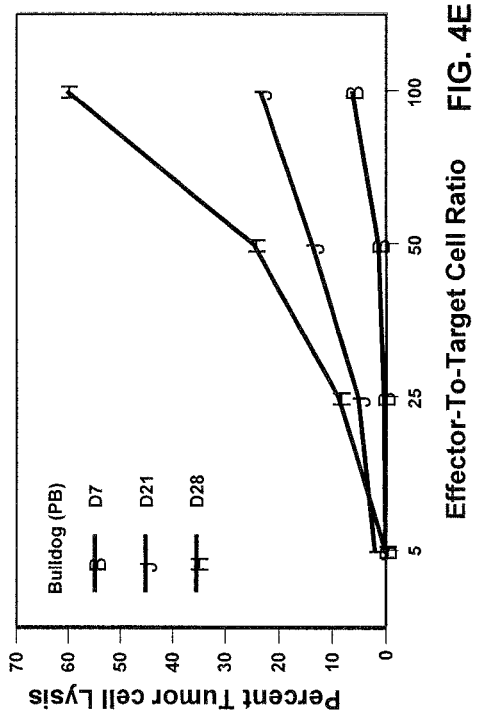
FIG. 4F shows cell mediated response in a Corgi.
Figure 4G:
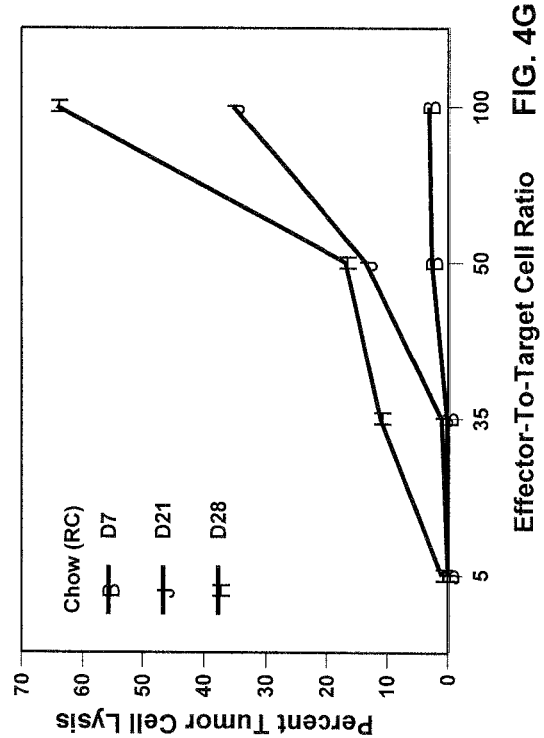
FIG. 4G shows cell mediated response in a Chow.

The humoral immune response was measured over time using Western blot and cellular immunity by in vitro cytotoxicity assays (FIG. 2). None of the 7 dogs in the study showed any adverse side-effects from the vaccine, while all dogs on the trial developed a highly significant antibody response to the cell vaccine priming antigen as well as a strong immune response to autologous tumor cells. In fact, the sera from all dogs exhibited antibodies to multiple tumor antigens. The sera from each dog also recognized tumor cells from all other canine breeds on the trial (Bulldog, Golden Retriever, Dachshund, Vizsla, Greyhound, Corgi and Chow). Cross reactivity of the humoral response to tumor cells from other breeds by immune sera from a Bulldog as shown by Western Blot analysis is shown in FIG. 3.

EXAMPLE 2

Clinical Assessment Criteria

Animals in this study were selected based on the following eligibility criteria listed in Table 3.

TABLE 3

No chemotherapy or wide field radiotherapy prior to beginning protocol therapy and no immunosuppressive therapy, including corticosteroids.
Patients can be any canine breed, age, sex in otherwise good health.
Patients must have staging diagnostic.
Normal organ and marrow function.
Patients must have an owner with the ability to understand and the willingness to sign a written informed consent document and comply with the protocol.

Animals were excluded from the study if any of the following exclusion criteria listed in Table 4 were met.

TABLE 4

Previous chemotherapy, radiotherapy, or corticosteroid therapy prior to entering the study.
Patients may not be receiving any other investigational agents.
History of allergic reactions attributed to compounds of similar chemical TABLE 4-continued or biologic composition to *Streptococcus pyogenes*.
Life-threatening illness unrelated to cancer.
Additional uncontrolled or active illness; other than lymphoma.

EXAMPLE 3

Preparation of Tumor Vaccines

Lymphoma cells isolated from tumor samples were transfected with the pcDNA3/emm55 plasmid by electroporation. Cells expressing the Emm55 antigen were selected in the presence of G418 and expanded to the required cell concentration. Prior to use the transfected cells were γ irradiated (10,000 rads, 30 minutes) then stored in liquid nitrogen in 2 ml DMEM supplemented with 10% DMSO and 20% FBS.

Immediately before injection of the vaccine, heparinized blood (20 ml) was drawn for in vitro immunological studies and for clinical pathology (full blood count and clinical chemistry). A urine sample was obtained for urinalysis for protein and blood. The disease was restaged in accordance with current guidelines, see Table 1. All vaccine doses were administered intravenously at a cell concentration of $1\times10^7$ in a volume of 2 ml. Subjects were monitored immediately following injection by veterinary staff and overnight for side effects compatible with an anaphylactic or other reaction to the medication; i.e., vomiting, diarrhea, collapse or shock. Any reaction was treated immediately.

Immediately before injection of the vaccine, heparinized blood (20 ml) was drawn for in vitro immunological studies and for clinical pathology (full blood count and clinical chemistry). A urine sample was obtained for urinalysis for protein and blood. The disease was restaged in accordance with current guidelines (See Table 1). All vaccine doses were administered intravenously at a cell concentration of $1\times10^7$ in a volume of 2 ml. Subjects were monitored immediately following injection by veterinary staff and overnight for side-effects compatible with an anaphylactic or other reaction to the medication (vomiting, diarrhea, collapse, shock). Any reaction was treated immediately.

EXAMPLE 4

Cell Vaccine Administration and Clinical Testing

Subjects complying with the entry criteria, see Example 1, were entered the study following the owner's informed consent. Subjects underwent to complete medical, physical, hematologic and biochemical examinations (Cell Blood Count, Serum Chemistry Panel, and Urinalysis) and diagnostic imaging (thoracic radiographs and abdominal ultrasound) to document general fitness and stage the disease to proceed with the trial. Tumor tissue was collected via fine needle aspirate or excisional biopsy of the lymph node at diagnosis or shortly thereafter and deposited into a sterile 15 ml conical tube containing 10 ml DMEM supplemented with 10% FBS.

Immediately before injection of the vaccine, heparinized blood (20 ml) was drawn for in vitro immunological studies and for clinical pathology (full blood count and clinical chemistry). A urine sample was obtained for urinalysis for protein and blood. The disease was restaged in accordance with current guidelines. All vaccine doses were administered intravenously at a cell concentration of $1\times10^7$ in a volume of 2 ml. Subjects were monitored immediately following injection by veterinary staff and overnight for side-effects compatible with an anaphylactic or other reaction to the medication (vomiting, diarrhea, collapse, shock). Any reaction was treated immediately.

The 7 dogs in the study were both male (5) and female (2) of various breeds; Bulldog, Vizsla, Greyhound, Golden Retriever, Dachshund, Corgi and Chow and their ages ranged from 4 to 11 years (Table 2). Autologous vaccine was produced for each dog from biopsies taken from regional lymph nodes. Animals were vaccinated approximately 2 weeks from the time of biopsy. The intravenous dose, $1\times10^7$ irradiated cells, was the same for all dogs. Each dog received weekly vaccine inoculations for a total of 4 weeks and in most cases went on to receive monthly doses.

Autologous tumor cells were isolated from tumor biopsies, transfected by electroporation with a plasmid vector containing the emm55 gene, selected on G418, expanded, γ-irradiated and reintroduced by intravenous injection at a cell concentration of $3\times10^7$ per vaccine dose. Three doses were given at 1 week intervals. The dogs were monitored for 24 hr post inoculation for adverse reactions. Sera and lymphocytes were collected at the time of each vaccination. The humoral immune response was measured over time using Western blot and cellular immunity by in vitro cytotoxicity assays. None of the 7 dogs in the study showed any adverse side-effects from the vaccine, while all dogs on the trial developed a highly significant antibody response to the cell vaccine priming antigen as well as a strong immune response to autologous tumor cells. In fact, the sera from all dogs exhibited antibodies to multiple tumor antigens. The sera from each dog also recognized tumor cells from all other canine breeds on the trial (Bulldog, Golden Retriever, Dachshund, Vizsla, Greyhound, Corgi and Chow).

Immediately before injection of the vaccine, heparinized blood (20 ml) was drawn for in vitro immunological studies and for clinical pathology (full blood count and clinical chemistry). A urine sample was obtained for urinalysis for protein and blood. The disease was restaged in accordance with current guidelines. All vaccine doses were administered intravenously at a cell concentration of $1\times10^7$ in a volume of 2 ml. Subjects were monitored immediately following injection by veterinary staff and overnight for side-effects compatible with an anaphylactic or other reaction to the medication (vomiting, diarrhea, collapse, shock). Any reaction was treated immediately.

EXAMPLE 5

Safety and Tolerability

The safety and tolerability of the vaccine was monitored according to the following toxicity guidelines used by the National Cancer Institute listed in Table 5.

TABLE 5

| | |
|---|---|
| Grade 0 | No adverse effects |
| Grade 1 | Mild symptoms: responsive to drugs and appropriate supportive measures, for example, mild fever, nausea, diarrhea, mild respiratory complications and/or mild respiratory distress that respond clinically to treatment. |
| Grade 2 | Moderate symptoms: responsive to drugs and appropriate supportive measures. Moderate signs/symptoms are similar to Grade 1, except they are moderate in nature. |
| Grade 3 | Severe symptoms: non-responsive to drugs and persisting for more than 24 hours. These sign/symptoms are criteria for pausing the study. For example, cardiac arrhythmia, certain infections, severe immunological or anaphylactic reactions and other severe but non-life-threatening system complications. |
| Grade 4 | Life-threatening events: These signs/symptoms are criteria for stopping the study. For example, high fever for more than 72 hours after vaccine delivery that is insensitive to anti-pyretics and not attributable to other causes and other extreme symptoms not attributable to other etiology. |
| Grade 5 | Fatal event |

Table 6 is a summary of canine information and timeline of protocol administration in the study. The lymphoma autologous cell vaccine was prepared and administered to each dog.

TABLE 6

| Breed | Age (Yrs) | Sex | Weight (kg) | Disease Stage | Vaccine Produced | Weekly Doses | Monthly Doses | Immune Response Humoral | CMI |
|---|---|---|---|---|---|---|---|---|---|
| Bulldog (PB) | 5 | Male | 28.2 | 4 | Yes | 4 | 0 | + | + |
| Golden Retriever (IR) | 11 | Female | 37.7 | 4 | Yes | 4 | 8 | + | + |
| Dachshund (PD) | 7 | Male | 6.2 | 3a | Yes | 4 | 1 | + | + |
| Vizsla (BV) | 4 | Male | 28.4 | 4/5 | Yes | 4 | 8 | + | + |
| Greyhound (JG) | 10 | Female | 32.2 | 4/5 | Yes | 4 | 7 | + | + |
| Corgi (AC) | 10 | Male | 16.4 | 4 | Yes | 4 | 2 | + | + |
| Chow (RC) | 10 | Male | 20.5 | 4 | Yes | 4 | 2 | + | + |

EXAMPLE 6

In Vitro Assessment

Western Blot Analysis

Western blot analysis was performed as a semi-quantitative measurement of tumor-specific antigens recognized by antibodies produced by each canine in response to the vaccine. An aliquot of the canine lymphoma tumor cells was lysed using 1 ml of a mammalian lysis buffer (Mammalian Cell-PE LB, Geno-Tech, St. Louis, Mo.). The cell lysates were then clarified by centrifugation and the supernatant harvested. The lysates were subjected to 12% SDS-Polyacrylamide gel electrophoresis. The loaded gels run at 200 V for 45 min. Transfer of the separated proteins from the gel to PVDF membrane was carried out using a BioRad Semi-dry Transfer system at 100 mA for 60 min. Following transfer the blot/PVDF membrane was washed overnight using 100 ml of Tween-Tris buffered saline (TTBS) with 1% non-fat dried milk.

The PVDF/blot was transferred to a glass hybridization cylinder and 15 ml of primary antibody (anti-Emm55 monoclonal antibody; clone 25C3) at a dilution of 1:5000 was added and the membrane incubated/rotated in a hybridization oven at 37° C. for 30 min. Following this incubation step, the PVDF/blot was washed 3 times in 15 ml of TTBS buffer. Following the final wash, 20 ml of a 1:20000 dilution of a sheep anti-mouse IgG (horseradish peroxidase labeled) was added and the PVDF/blot incubated for a further 30 min at 37° C. The PVDF/blot was then washed 3 times in TTBS. Detection of the bound antibody was carried out using Amersham's ECL Western Blotting Analysis System in accordance to the manufacturer's instructions. Detection of labeled bands was carried out by placing the PVDF/blot on an X-ray film and exposing the film for varying times depending on the signal strength of the blot.

EXAMPLE 7

Cellular Cytotoxicity Assay

The cellular immune responses to autologous tumor cells were evaluated using a non-isotopic-based cell-mediated immunity (CMI) assay. Briefly, suspensions of Ficoll-purified canine peripheral blood lymphocytes were prepared from the test samples. The cells were resuspended in RPMI 1640 supplemented with 10% FBS, 2-mercaptoethanol, and HEPES. The lymphocytes, at $5 \times 10^6$ cells/well, were then incubated with stimulator cells ($2 \times 10^5$ autologous tumor cells treated with 100 μg/ml mitomycin C for 30 min at 37° C.). Plates were then incubated at 37° C. in a humidified 5% $CO_2$ atmosphere for 6-to-7 days to expand tumor-specific effector cells. To measure cytotoxicity against tumor cell targets, effector cells were harvested following in vitro stimulation for 6-7 days and incubated with target cells at various effector-to-target ratios in a non-radioactive cytotoxicity assay, CYTOTOX 96 (Promega).

FIG. 4 shows the cell-mediated response in individual dogs at day 0, 21, and 28. The data show that dogs receiving autologous cell vaccine produced a strong cellular response to their own tumor cells. The response increased over time.

Figure 5:
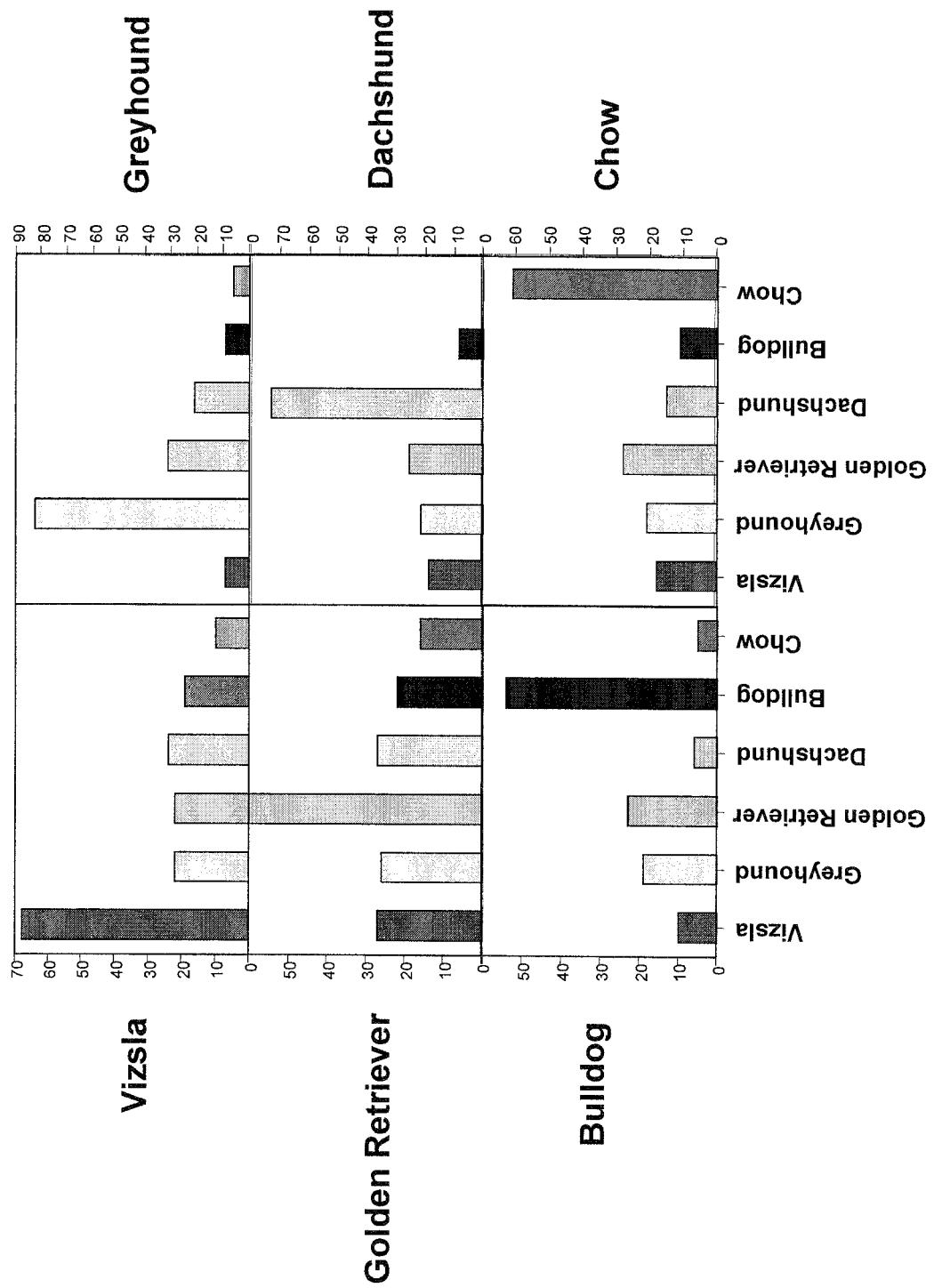
FIG. 5 is a composite graph for 6 dogs illustrating the vaccine induced cross reactive cellular response. Effector cells from vaccinated dogs (Y-axis) were reacted against autologous and heterologous target tumor cells (X-axis). The Y-axis also represents percent lysis as measured in a short-term CMI assay.

Effector cells from vaccinated dogs were reacted against autologous and heterologous target tumor cells. The graph in FIG. 5 represents the percent lysis as measured in a short-term CMI assay.

Table 7 shows cellular response induced by autologous cancer cell vaccine in dogs by their own tumors. The response was significantly higher than that observed against heterologous targets (other breeds). The lymphocytes were used at an effector to target cell ratio of 100:1 in a short-term non-radioisotopic CMI assay. The autologous CMI responses are in bold.

TABLE 7

| Target Cell Origen | Vizsla | Greyhound | Golden Retriever | Dachshund | Bulldog | Chow |
|---|---|---|---|---|---|---|
| Vizsla | 68% | 9% | 27% | 18% | 10% | 18% |
| Greyhound | 22% | 82% | 26% | 21% | 19% | 21% |
| Golden Retriever | 22% | 31% | 60% | 25% | 23% | 28% |
| Dachshund | 24% | 21% | 27% | 71% | 6% | 15% |
| Bulldog | 19% | 9% | 22% | 8% | 54% | 11% |
| Chow | 10% | 6% | 16% | 0% | 5% | 61% |

Preparation and testing of Emm55 vectors, cloning, analysis and transformation are described in detail in U.S. patent application Ser. No. 10/964,471 which is incorporated herein by reference in its entirely.

EXAMPLE 8

Gene Transfer by Electroporation

The cells were harvested and washed twice with incomplete IMDM. In order to facilitate the expression of the Emm55 antigen in tumor cells, the pcDNA3/emm55 plasmid was introduced by electroporation. DNA samples were resuspended prior to transfection in 2× Hanks balanced salts buffer (1.4 mM $Na_2HPO_4$, 10 mM KCl, 12 mM glucose, 275 mM NaCl and 40 mM HEPES, pH 7.2). Tumor cells tested were electroporated using 20 μg plasmid DNA at 260 V and 1050 μF for $1 \times 10^6$ tumor cells. Since the pcDNA3 vector backbone carries a neo cassette, stable transfectants can be selected with G418. The most effective concentration of G418 for selecting stably transfected cells was determined to be 500 μg/ml.

pSVK3/emm55 was transfected into lymphoma cells by electroporation. The cells were prepared for gene transfer as previously described except that the number of cells used for each reaction was $2 \times 10^6$/ml. pSVK3/emm55 was linearized before transfection with Bam HI (10 units/μl). Twenty pg DNA was resuspended in $H_2O$ and used for each electroporation reaction. Electroporation was carried under three different conditions: 220V, 1050, pt.F; 260 V, 1050 ILIF; and 300 V, 1050 Following electroporation, the cells were plated on the 9 wells culture plates and 5 ml of complete IMDM was added. Gene expression was measured by flow cytometry after 72 hours and 11 days. In order to obtain stably transfected cells, Neuro-2a cells were electroporated with 20 μg each of pSGINEOpA and pSVK3/emmL 55 at 260 V and 1050 [if. Cells were cultured under conditions as described for gene transfer of pcDV 1/a and pcDV.

Morphological Characteristics of Stable Transfected Cell Lines

Introduction of the vectors into cells changed the cell morphology. The transfected cells selected by G418 grew in characteristic clumps, whereas the untransfected cells formed an even monolayer. This is not due to the presence of G418 in the medium since inhibition assay experiments did not show morphological changes in the presence of the drug.

Tumor Cell Inoculation

Untransfected lymphoarcoma cells transfected with emm55 were prepared for inoculation by gently removing them from 75 $cm^2$ tissue culture flasks with a sterile cell scraper. The cell suspension was harvested by centrifugation at 800×g and the resulting pellet resuspended in incomplete IMDM.

What is claimed is:

1. A vaccine composition for treating advanced stages of mammalian lymphoma comprising isolated autologous or non-autologous lymphoma cells transformed with an expression vector comprising a nucleic acid having the sequence of SEQ ID NO: 1 encoding a *Streptococcus pyogenes* Emm55 polypeptide operably linked to a promoter in a pharmaceutically acceptable excipient.

2. The vaccine of claim 1 wherein the lymphoma cells are transfected with a plasmid vector comprising a nucleic acid having the sequence of SEQ ID NO: 1.

3. The composition of claim 1 wherein the lymphoma cells are canine.

4. The autologous or non-autologous lymphoma cells of claim 1 wherein the expression vector further comprises a drug resistance gene.

5. The autologous or non-autologous lymphoma cells of claim 1 wherein the drug resistance gene is a neomycin resistance gene.

6. The autologous or non-autologous lymphoma cells of claim 5 which are canine.

7. The autologous or non-autologous lymphoma cells of claim 1 wherein the cells are irradiated prior to transformation with said expression vector.

8. The autologous or non-autologous lymphoma cells of claim 1 wherein the transformation is by electroporation of said nucleic acid.

9. The lymphoma cell vaccine of claim 1 wherein the isolated mammalian lymphoma cells are human.

* * * * *

SEQUENCE LISTING

<160> NUMBER OF SEQ ID NOS: 2

<210> SEQ ID NO 1
<211> LENGTH: 900
<212> TYPE: DNA
<213> ORGANISM: Streptococcus pyogenes

<400> SEQUENCE: 1

```
atggctaaaa ataccacgaa tagacactat tcgcttagaa aattaaaaac aggaacggct    60
tcagtagcag tagctttgac tgttttaggg acaggactgg tagcagggca gacagtaaaa   120
gcaagccaaa cagaaccatc tcagaccaat aacagattat atcaagaaag caacgttta   180 caggatttaa aaagtaagtt tcaagacctg aaaaatcgtt cagagggata cattcagcaa   240
tactacgacg aagaaaagaa cagtggaagt aactctaact ggtacgcaac ctacttaaaa   300
gaattaaatg acgaatttga acaagcttat aatgaactta gtggtgatgg tgtaaaaaaa   360
ttagctgcaa gtttgatgga agaaagagtc gctttaagag acgaaatcga tcagattaag   420
aaaatatcag aagaattaaa aaataagctg agagcaaaag aagaagaatt aaaaaataaa   480
aaagaggaac gtgagcttga gcatgctgcc tatgcagcag atgcaaagaa acatgaagaa   540
tatgtcaaat ccatgtctct cgctactaat ggataaagaa gaggagcgct cataaactag   600
agcaatcatt agacacggct aaagctgagc ttgttaaaaa agagcaagag ttacagttag   660
tcaaaggcaa tctagatcaa aaagaaaaag aactagaaaa tgaagagcta gcgaaagaaa   720
gtgctattag tgatttgact gagcagatta ctgctaagaa ggctgaagta gaaaaattaa   780
ctcaagattt agcctgctaa gtctgctgaa attcaggaaa aagaagctga aaagatcgc    840 caacagcata tgtacgaagc gtttatgagc cagtacaaag aaaaagttga gatacaagag   900
```

<210> SEQ ID NO 2
<211> LENGTH: 787
<212> TYPE: DNA
<213> ORGANISM: Streptococcus pyogenes

<400> SEQUENCE: 2

```
gttttcttct atgcgtttta caactgctgc tactccagct gttgccataa cagtaagggc    60
tgccgctgta aagaatggat tagctgcttc acctgttgat ggtaactgtc tcttagtttc   120
cttcattggt gctttgtttt ggttaggttt tgtgcctgct tgtggtgctt gacctgtacc   180
tggaacaact ttgtttcctg gttttgcatc aggggtttgt gagtctgatg cttttccagc   240
tgcttcaagt ttcgcttgta gctcagcttt ttcttttttct gttaatttct tgctttcttc   300
aagctctttg ttaagttttt caagagccgc taatttgctg tttgcttctt ctaaagcttt   360
ttcaacttgt ttcttagctt cacgtgatgc gtccaagtca cgacgaagac ctttacggct   420
tgcgtctgaa atttgtttat cttctttaac cttatcaagt tcagcagtca agtttgctaa   480 atcttttttca acttgtttct tagcttcacg tgatgcgtcc aagtcacgac gaagaccttt   540
acggctcgct tctgaaatct tgttttgttc ttcaagtttt gctttgtcgc ttgctaattg   600
ttcattttca gcagacaact tagctatcat atccttagca ttacctaata gattgttgtt   660
gatggtttca agttgtttta gcttagcaag ctcttgctct tgtttctcaa cttttttcttt   720 gtactggctc ataaacgctt cgtacatatg ctgttggcga tcttttttcag cttctttttc   780 ctgaatt                                                              787
```